US008955520B2

(12) United States Patent
Devereux et al.

(10) Patent No.: US 8,955,520 B2

(45) Date of Patent: Feb. 17, 2015

(54) METHOD OF PLACING MULTIPLE BILIARY STENTS WITHOUT RE-INTERVENTION, AND DEVICE FOR SAME

(75) Inventors: Paul Devereux, Dublin (IE); Ciarán Toomey, Rathcormac (IE); Sharon White, Wexford (IE)

(73) Assignee: Cook Medical Technologies LLC, Bloomington, IN (US)

(*) Notice: Subject to any disclaimer, the term of this patent is extended or adjusted under 35 U.S.C. 154(b) by 5 days.

(21) Appl. No.: 13/553,165

(22) Filed: Jul. 19, 2012

(65) Prior Publication Data

US 2014/0025149 A1 Jan. 23, 2014

(51) Int. Cl.
*A61F 2/04* (2013.01)

(52) U.S. Cl.
USPC ...... 128/898; 623/1.11; 623/1.27; 623/23.64; 623/1.16

(58) Field of Classification Search
USPC ........................................................ 623/1.27
See application file for complete search history.

(56) References Cited

U.S. PATENT DOCUMENTS 5,669,924 A * 9/1997 Shaknovich ................. 623/1.11
7,229,472 B2 * 6/2007 DePalma et al. ............. 623/1.16
2004/0220664 A1 * 11/2004 Chobotov .................... 623/1.23
2005/0125050 A1 * 6/2005 Carter et al. ................. 623/1.11
2006/0142704 A1 * 6/2006 Lentz ............................ 604/264
2008/0033521 A1 * 2/2008 Jorgensen et al. ........... 623/1.11
2012/0016454 A1 * 1/2012 Jantzen et al. ............... 623/1.11

OTHER PUBLICATIONS

Hamada, Tsuyoshi et al., "Anchor-wire technique for multiple plastic biliary stents to prevent stent dislocation," World Journal of Gastroenterology, vol. 17, Issue 28, Jul. 28, 2011, pp. 3366-3368.
Leung, Joseph, "Use of the FUSION system for Multiple Biliary Stenting," Cook Medical, www.cookmedical.com, © 2011, 3 pages.

* cited by examiner

*Primary Examiner* — Thomas J Sweet
*Assistant Examiner* — Rebecca Preston
(74) *Attorney, Agent, or Firm* — Brinks Gilson & Lione

(57) ABSTRACT

A dual lumen catheter may be provided with one or more stents in a stent-deployment lumen and a wire guide disposed through a wire guide lumen. The wire guide may be directed to a target site in a patient body such as a biliary stricture. The catheter may be directed along the wire guide until it is in or adjacent the target site. A distalmost stent may be advanced out a distal side-facing aperture of the stent-deployment lumen into the target site by a pusher member that advances the stent or that holds the stent in place while the catheter is proximally withdrawn from around the stent. With the wire guide remaining substantially in place, the stent-deployment lumen can be reoriented and the steps repeated to place a second (and, if desired, subsequent) stent(s) next to—and generally parallel with—the first stent.

10 Claims, 6 Drawing Sheets

METHOD OF PLACING MULTIPLE BILIARY STENTS WITHOUT RE-INTERVENTION, AND DEVICE FOR SAME

TECHNICAL FIELD

Embodiments disclosed herein generally relate to a method for placing a plurality of biliary stents across a stricture. More particularly, embodiments relate to a method and device for placing a plurality of biliary stents without requiring re-introduction of a stent delivery catheter.

BACKGROUND

Endoscopic retrograde cholangiopancreatography (ERCP) is a technique used for viewing and treating the ducts that drain the liver and pancreas. Biliary ducts form a drainage routes into the duodenum from the liver and gallbladder and they join the pancreatic duct, just before they drain into the duodenum about 3 inches from the stomach. The drainage opening is called the papilla (Ampulla of Vater). The papilla is surrounded by a circular muscle, called the sphincter of Oddi. During ERCP, X-ray contrast dye is injected into the bile duct, the pancreatic duct, or both via a catheter disposed through a working channel of an endoscope.

Two commonly used types of catheters used during ERCP procedures (particularly where a catheter may be exchanged) are referred to as "long-wire" catheters and "short-wire" catheters. A long-wire catheter is one in which a wire guide lumen is provided through the major length of the catheter. That is, in a catheter configured for use with long-wire procedures, the wire guide lumen extends through more than half, most, or all of the catheter's length. In catheters for short-wire procedures, the wire guide lumen may not extend the entire length of the catheter. In this type of catheter, the wire guide lumen may extend only from the distal end of the terminal-end device to a point intermediate the distal and proximal ends of the catheter, and often the wire guide extends through less than half or only a very small percentage of the catheter's length (defined herein as a minor length). This shorter lumen is the only portion of the catheter encompassing the wire guide during a short wire operation.

The decreased friction and the lack of a need for a wire guide that is at least about twice as long as the catheter are generally considered advantages of a short-wire catheter, although the pushability of a catheter without a wire guide engaged into a long-wire lumen may be less than that of a long-wire catheter so engaged. Short-wire catheters are often easier to exchange than catheters having the wire guide lumen extending the entire length of the catheter. This is because the wire guide need not be as long as a "long wire" configuration, which requires that a length of the wire guide extending outside the patient's body be longer than the portion of the catheter extending over the long wire guide in order for a doctor or assistant to maintain a grasp on the wire guide (to avoid undesired movement or displacement thereof). The short wire guide configuration catheters (known also as "rapid exchange catheters) also create less friction during mounting and exchange operations due to the shorter wire guide lumen, leading to a reduced likelihood of displacing the wire guide after it has been positioned, often under radiography, to a desired position/orientation.

Stents may be placed into the bile and/or pancreatic ducts to bypass strictures of the duct. These narrowed areas of the bile or pancreatic duct may be caused by—for example—inflammation, scar tissue, or tumors that cause blockage of normal duct drainage. Metal and/or plastic stents may be used, depending upon the medical indications. In some circumstances, it may be useful to provide a plurality of stents that cross a single stricture in generally parallel fashion, such as is shown—for example—in FIG. 1. The example of FIG. 1 shows two plastic biliary stents 197, 199 disposed through a biliary duct 182 and protruding through the Ampulla of Vater 184 (not to scale) into the duodenum. Such stents typically are placed by being directed to a target site over and along a guide catheter disposed through the stent lumen.

Placement of multiple biliary stents in bile duct stricture can be technically challenging, because difficulties may arise from accessing the stricture with repeated cannulation and guide wire placement. The subsequent exchanges done over a very long guide wire may increase the procedural complexity. In the conventional manner of delivering multiple stents to traverse a single stricture, repeated bile duct cannulation and exchanges are necessary in order to place multiple stents to attain the maximum lumen diameter for the stricture. Direct cannulation with the stent preloaded on stent-delivery catheter without a prior inserted wire guide may be difficult. Although it is possible to use a single wire guide left in place to direct a first (optionally pre-loaded) stent-delivery catheter to a target site, withdraw the stent-delivery catheter, recannulate the stricture, then re-introduce the same (reloaded) or a different (preloaded) stent-delivery catheter for placement of a second stent (repeated for any subsequent stent-placement), it would be advantageous to provide a system and method for serially placing a plurality of stents that would not necessitate the time, effort, and complexity of withdrawing and reintroducing a stent-delivery catheter for second and subsequent stents targeted to traverse a single stricture or to otherwise be delivered along a single wire guide.

BRIEF SUMMARY

In one aspect, embodiments disclosed herein may include a stent-delivery catheter, as well as methods for introducing a plurality of stents therethrough to a target site in a body passage, using a novel wire-guided technique wherein the stent does not encompass the wire.

In certain embodiments, the method may allow generally parallel placement of a plurality of stents during a single procedure, which may be an ERCP procedure.

DETAILED DESCRIPTION

Figure 1:
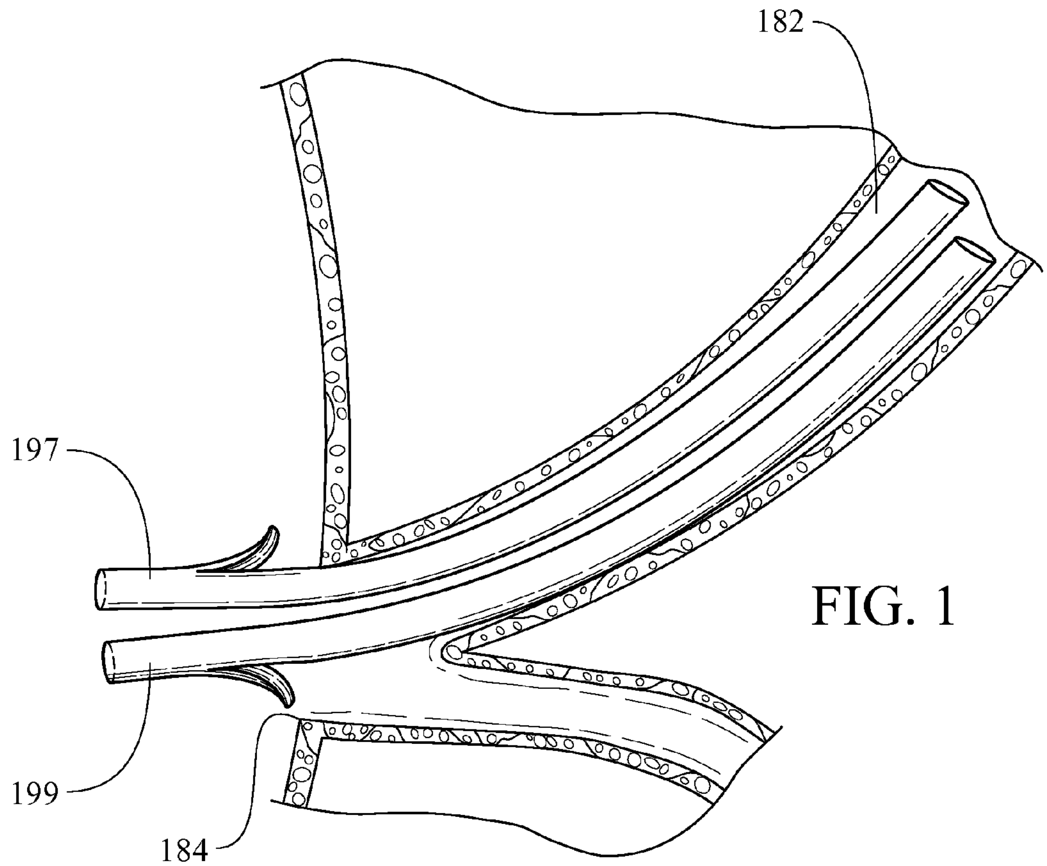
FIG. 1 shows a biliary duct structure traversed by two plastic biliary stents.

As used in the specification, the terms proximal and distal should be understood as being from the perspective of a physician operating a device embodiment and method herein for delivering a stent to a patient. Hence, the term "distal" means the portion of the delivery system that is farthest from the physician and the term "proximal" means the portion of the delivery system that is nearest to the physician. Also, as used herein unless otherwise specified, the term "end" refers to a region at and near a proximal or distal terminus, while the word "terminus" is used to refer to the absolute ends of the device defining where its construction ceases.

Embodiments are described with reference to the drawings in which like elements are generally referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

Various embodiments will be described more fully hereinafter. The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. Visualization of this procedure may be done using radiography and/or ultrasound, as stent construction materials, catheter construction materials, and operating procedures needed for effecting the presently disclosed method are within the skill of those in the relevant art. The method and device embodiments described herein may be used via an endoscope such as—for example—a transesophageal endoscope, percutaneously (via a laparoscope, associated trocar, or other percutaneous access device), in some combination thereof, or via other means, with preferable use being with minimally invasive surgical methods and devices.

Figure 2:
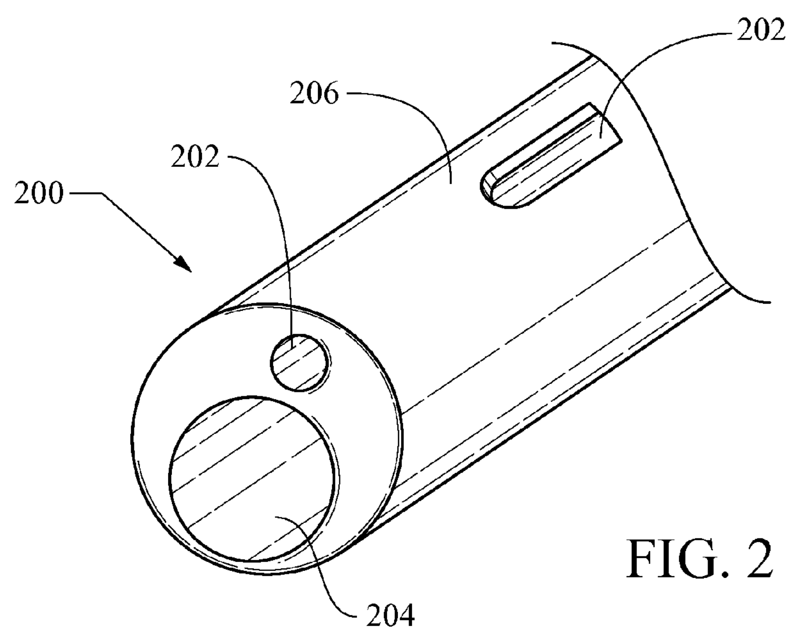
FIG. 2 shows one embodiment of a dual-lumen stent-delivery catheter.
Figure 3A:
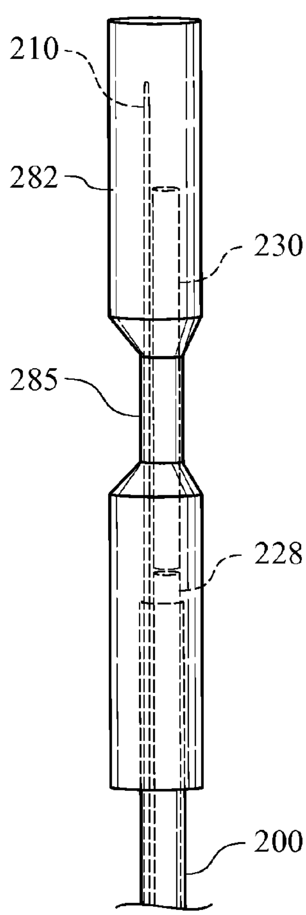
FIGS. 3A-3E show steps of a method for deploying a second stent into a body passage target site with the embodiment of FIG. 2.
Figure 3B:
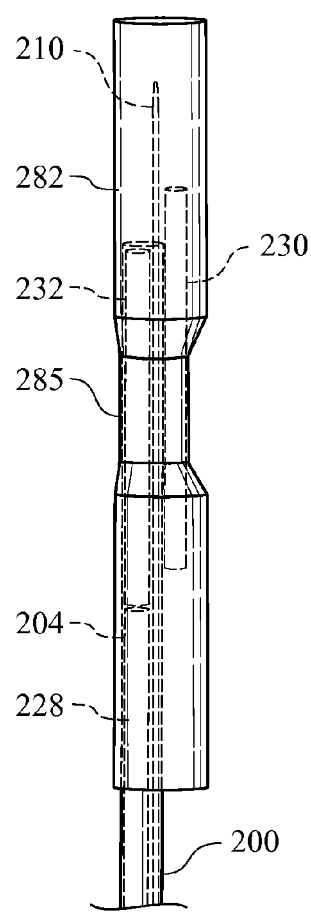
Figure 3C:
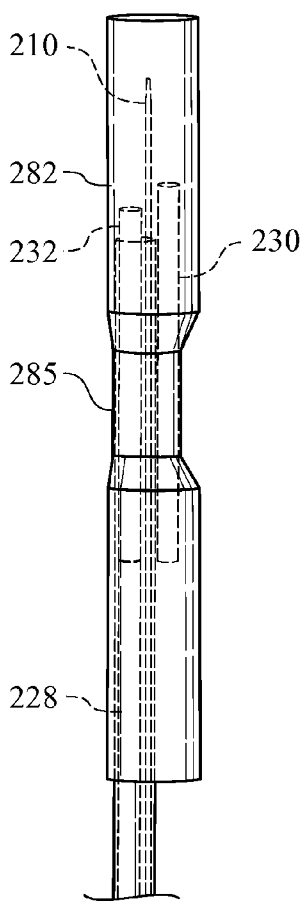
Figure 3D:
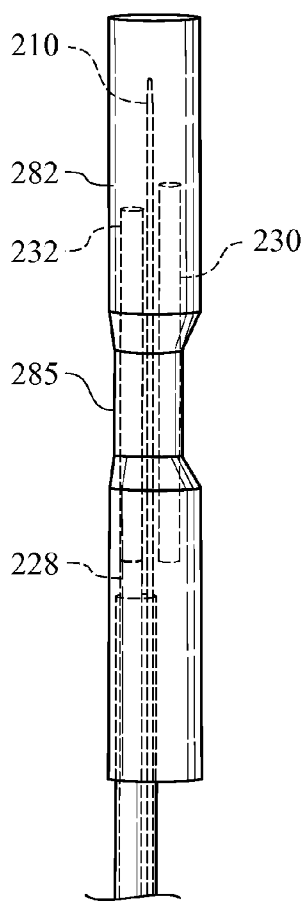
Figure 3E:
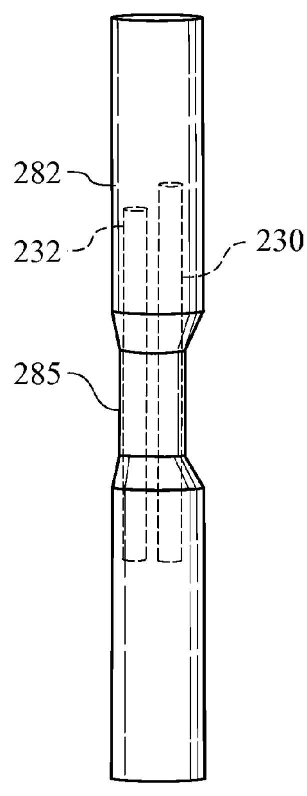

Embodiments of a device and method for placement of multiple stents (e.g., plastic biliary stents) are described here with reference to FIGS. 2-3E. FIG. 2 shows a dual-lumen catheter device 200. The catheter 200 includes a first lumen configured as a wire guide lumen 202 and a second lumen configured as a stent-delivery lumen 204, which extends through a major length of the catheter body 206 that defines lateral walls of each lumen. The wire guide lumen 202 may also extend through a major length of the catheter body (e.g., for use in a long-wire procedure) and/or it may include an opening (202*a*) through the side of the catheter body only a minor length away from the distal terminus of the catheter body (e.g., for use in a short-wire procedure). As such, the entire length of the wire guide lumen 202 may be directed through and occupy a major length and/or a minor length of the catheter body (i.e., short-wire, long-wire, or dual-use configuration). As is known in the art, a major length wire guide lumen may be provided with a side aperture through the catheter body a minor distance from the distal terminus of the catheter body. This latter configuration is commonly referred to as a "dual use" configuration, because it allows operation in either of a short wire or long wire procedure.

Figure 2A:
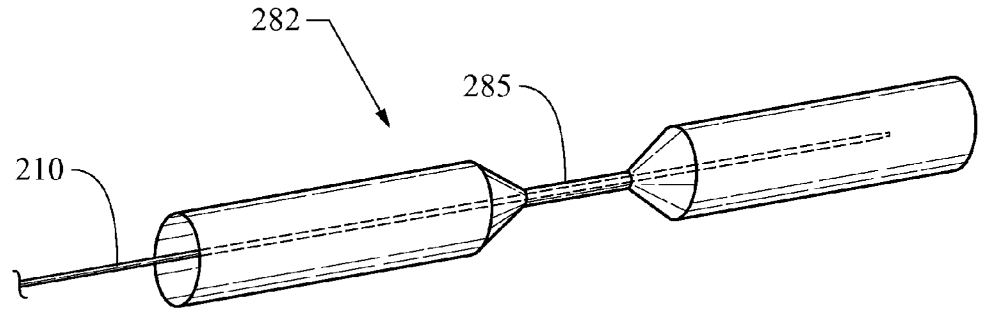
FIGS. 2A-2E show steps of a method for deploying a stent into a body passage target site with the embodiment of FIG. 2.
Figure 2B:
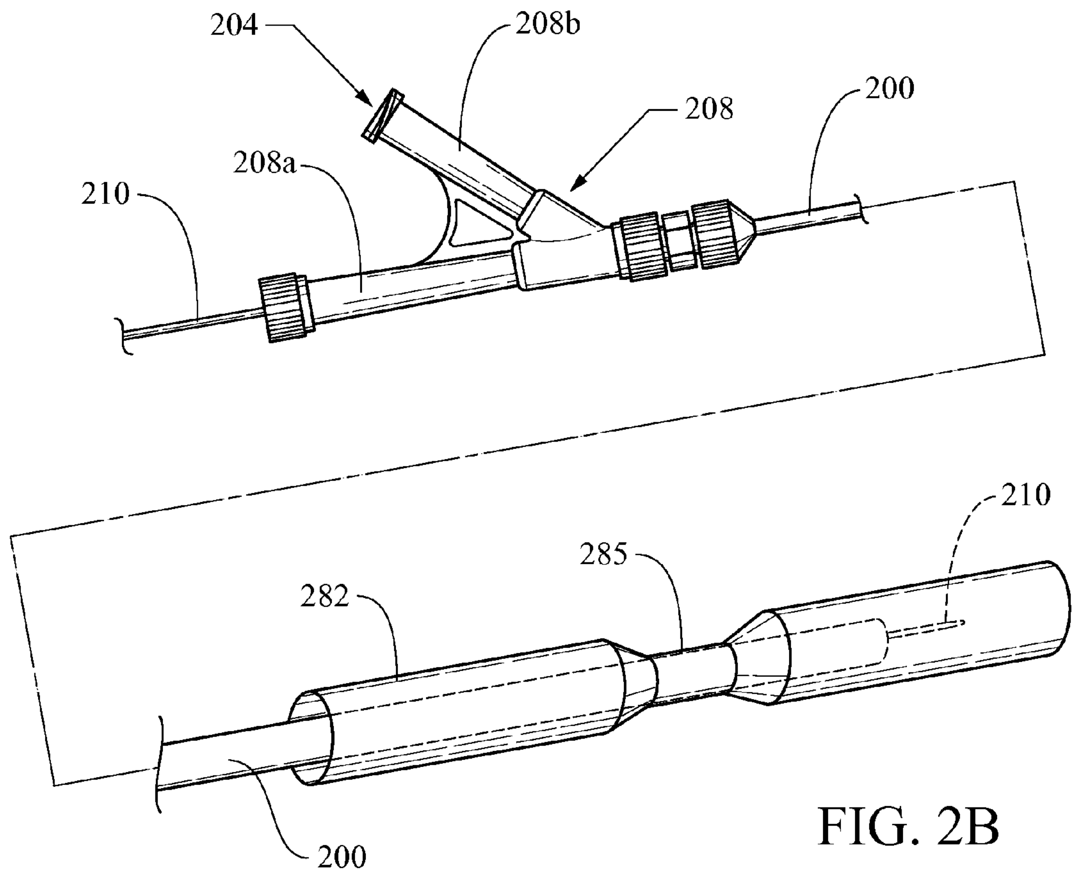

FIG. 2A shows a diagrammatic/schematic illustration of a duct (e.g. such as a biliary duct) 282 with an obstruction shown here as a stricture region 285. The diagrammatic illustrations provided will be understood by those of skill in the art as generally representative, but actual structures will most likely include far less geometric contours (e.g., a stricture may appear more like the passages shown in FIG. 1, the stent(s) may be curved and include one or more pigtails, flared apertures or other features, etc.). A wire guide 210 is shown as already having been introduced to traverse the stricture 285. In FIG. 2B, the catheter 200 has been directed along the wire guide 210 (which is disposed through the wire guide lumen 202). FIG. 2B also shows a proximal end configuration of one embodiment. This is shown as a y-shaped connector 208 with one arm 208*a* in communication with the wire guide lumen 202, and the other arm 208*b* in communication with the stent lumen 204 (although it should be appreciated that either arm could be configured in communication with either lumen, and different connector or introducer structures may be used within the scope of the present disclosure). A distal length of the catheter 200 is shown as having been directed along the wire guide 210 to a position proximally adjacent of, then having traversed, the stricture 285.

Figure 2C:
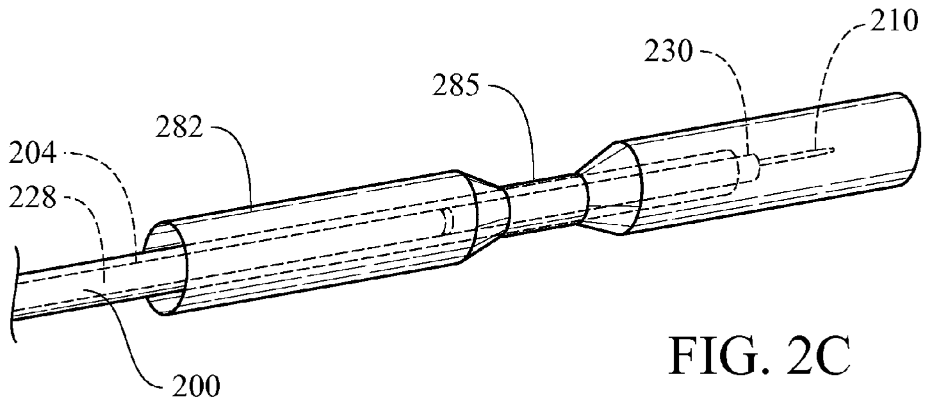
Figure 2D:
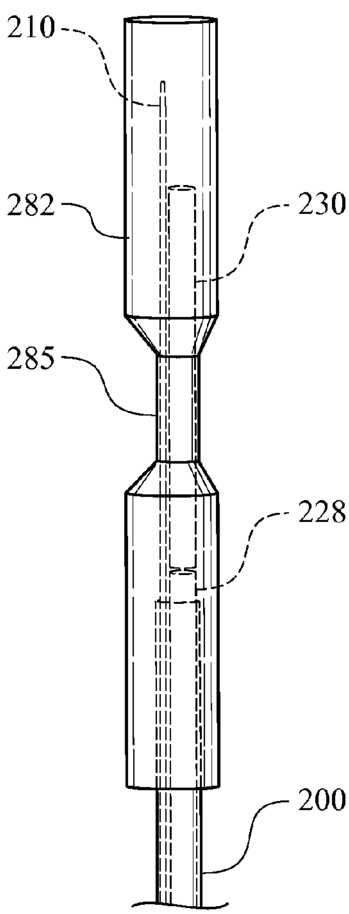
Figure 2E:
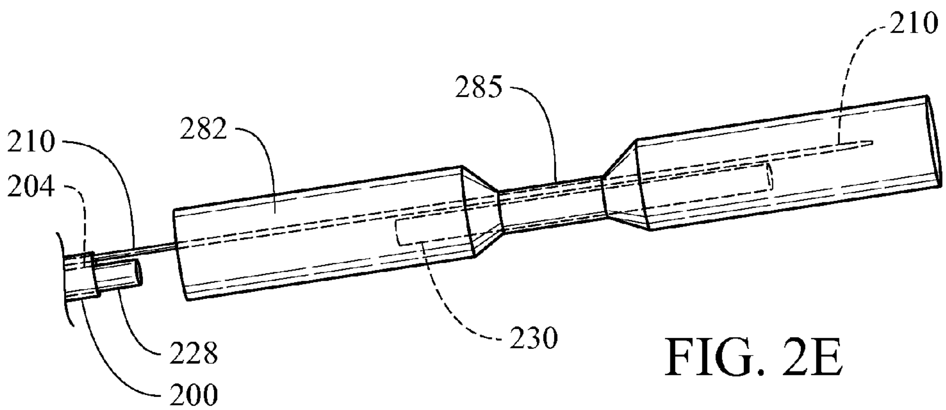

In FIG. 2C, a stent pusher 228 has been used to advance a polymeric biliary stent 230 through the stent lumen 204 portion traversing the stricture 285 so that the stent 230 traverses the stricture 285 while still within the lumen 204. It should be appreciated that metallic, metal/polymer, and other stent constructions known in the art or developed in the future may be practiced within the scope of the presently disclosed methods. Preferred stents may include polymeric or metallic stents (including, for example, stents having one or more pigtails, one or more flaps of the type shown in the present non-limiting illustrations, a coiled wire construction, or other features). The stent 230 is alongside but does not at all encompass the wire guide 210. Next, as shown in FIG. 2D, the catheter 200 may be withdrawn proximally while the stent pusher 228 and the wire guide 210 are each held in place. In this manner, the catheter 200 may be withdrawn from around the stent 230, leaving the stent 230 to traverse the stricture 285 and provide a path of fluid communication therethrough. The wire guide 210 also remains in its position (traversing the stricture 285) after placement of the stent 230, as shown in FIG. 2E.

Deployment of a second stent 232 is described with reference to FIGS. 3A-3E, which deployment method may be used to deploy further stents as well, in a serial manner without having to remove and "reload" a deployment apparatus. FIG. 3A shows the deployed first stent 230 as in FIG. 2E, with the catheter having been rotated so that the stent deployment lumen 204 is no longer aligned with the first stent 230. Next, as shown in FIG. 3B, the catheter 200 is again advanced along the wire guide 210 so that a distal end length thereof traverses the stricture 285. A second stent 232 is advanced through the stent lumen 204 by the stent pusher 228 until—within the confines of the stent lumen 204—the second stent 232 also traverses the stricture 285, as shown in FIG. 3C.

In the same manner as was used to deploy the first stent 230, and as shown in FIG. 3D, the catheter 200 may be withdrawn proximally while using the stent pusher 228 to hold the second stent 232 in a position traversing the stricture 285. As such, the second stent 232 is disposed across the stricture 285 alongside the first stent 230 and the wire guide 210 (without encompassing any portion of the wire guide 210). As shown in FIG. 3E, when all desired stents have been placed (e.g., two, three, or more stents as desired have been placed by treating personnel), the catheter 200 and wire guide 210 may be withdrawn leaving the stents 230, 232, et seq in place. As shown in FIG. 3E, it may be helpful to have the ends of the stents offset from one another to help positioning and alignment of the catheter 200 (e.g., during the procedure shown in FIGS. 3A-3D) for stent deployment. Various polymeric stents may be used with the device and method described herein, including those with one or more pigtail features, one or more retention/drain flaps, and/or flared stent designs. It should be appreciated that, in the diagrammatically simplified illustrations provided the stents are shown as occupying less than the full cross-sectional area of the stricture 285; however, in actual biological conditions, the stents will most likely occupy and expand a significant cross-section thereof. It should also be appreciated that the second stent (and, if provided, subsequent stents) may be provided—lined up seriatim—in the device lumen, where the pusher 228 engages the proximal-most stent and is used to advance the more distal stents until each is deployed as desired. The stents may include radio-opaque markers and/or radio-opaque construction.

Figure 4A:
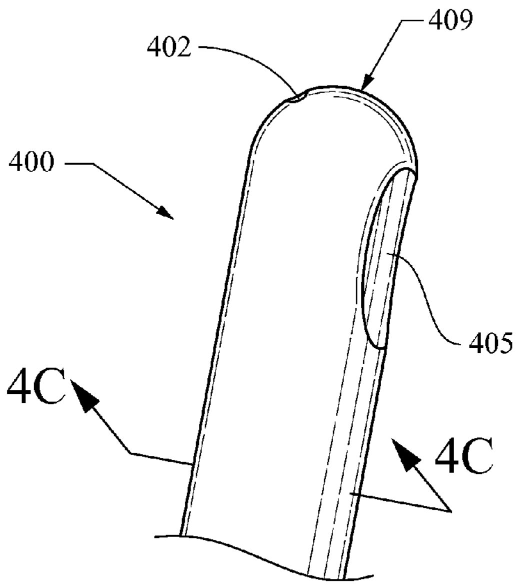
FIGS. 4A-4C show a long-wire embodiment of a dual-lumen stent-delivery catheter.
Figure 4B:
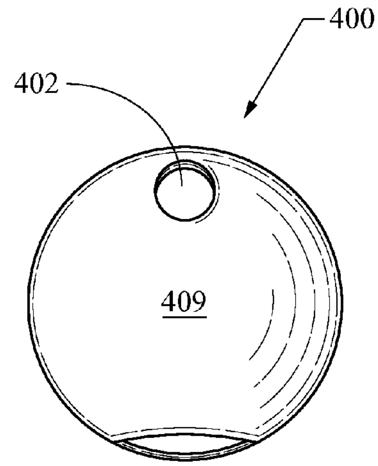
Figure 4C:
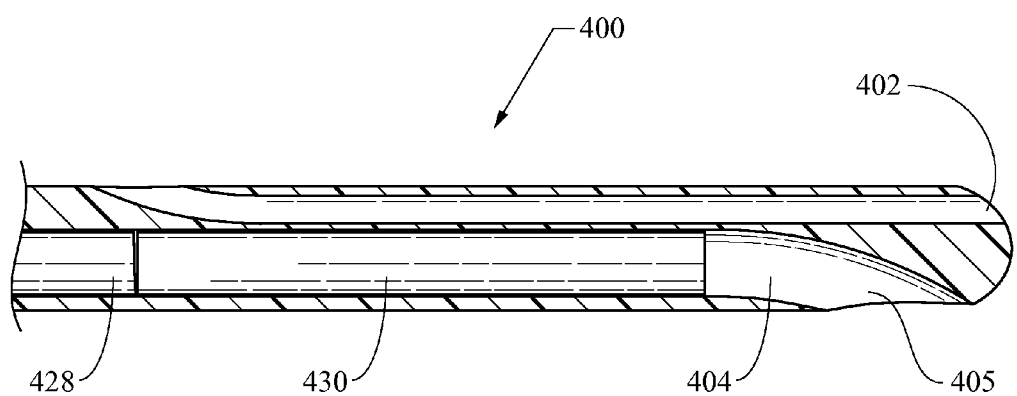

FIGS. 4A-4C show views of the distal end of another catheter embodiment 400. The face defining the distal terminus 409 is rounded to present an atraumatic, generally domed profile (viewed from the side in FIG. 4A, and end-on in FIG. 4B), which may ease direction of the catheter 400 through an endoscope working channel and/or through a body passage such as, for example, a biliary duct. The stent introducing catheter 400 includes a wire guide lumen 402 that is configured as a long-wire lumen extending longitudinally through a major length of the catheter 400. The catheter 400 includes a stent delivery lumen 404 that extends through a major length of the catheter body. A distal opening 405 of the stent lumen 404 is disposed along a longitudinal side of the catheter body (rather than, for example, facing out the distal terminus in the manner of the catheter 200 shown in FIG. 2). FIG. 4C, a longitudinal section view along line 4C-4C of FIG. 4A, illustrates an example of a polymeric biliary stent 430, which is shown as already positioned in the stent lumen 404. A stent pusher 428 (which may be solid or hollow) is disposed proximal of the stent 430. The stent pusher 428 is configured to pushingly contact and advance the stent 430 through the length of the stent lumen 404, and to hold it in place while the catheter is retracted (and/or to advance the stent distally) for stent deployment. A transition from a longitudinal length of the stent lumen 404 to the distal opening 405 is curved to provide for smooth exit of the stent 430 from the stent lumen 404.

Figure 5A:
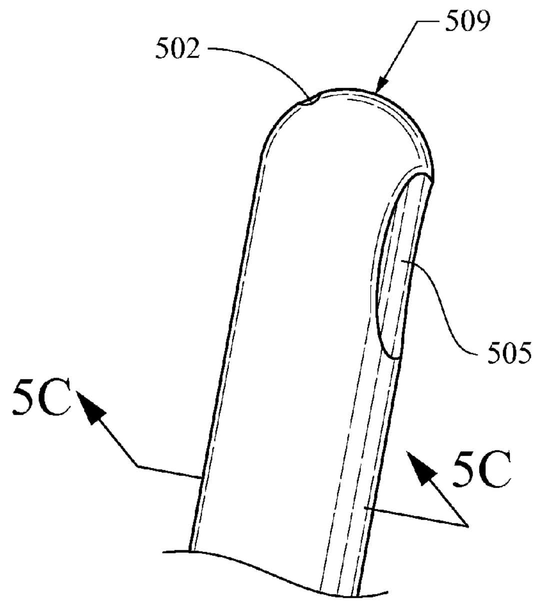
FIGS. 5A-5C show a short-wire embodiment of a dual-lumen stent-delivery catheter.
Figure 5B:
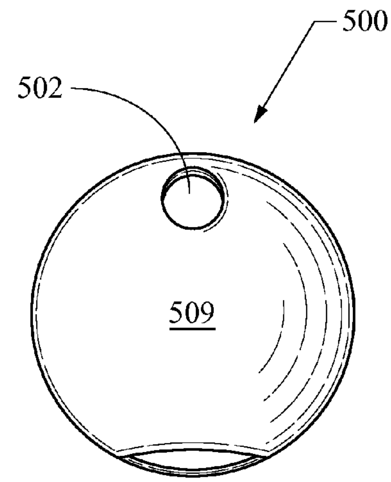
Figure 5C:
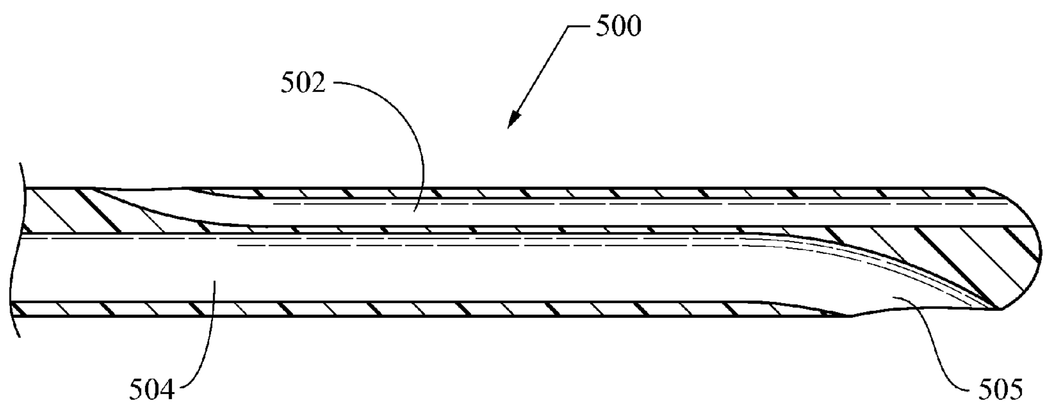

FIGS. 5A-5C show another stent delivery catheter embodiment 500, which is configured for use in a short wire procedure. The face defining the distal terminus 509 is rounded to present an atraumatic profile (shown end-on that may ease direction through an endoscope working channel and/or through a body passage such as, for example, a biliary duct. FIG. 5C, a longitudinal section view along line 5C-5C of FIG. 5A, illustrates that the catheter 500 includes a wire guide lumen 502 configured as a short wire lumen extending longitudinally through a minor length of the catheter 500. As such, a wire guide can be directed through the wire guide lumen 502 with minimal frictional contact. The catheter 500 includes a stent delivery lumen 504 that extends through a major length of the catheter body. A distal opening 505 of the stent lumen 504 is disposed along a longitudinal side of the catheter body (rather than, for example, facing out the distal terminus in the manner of the catheter 200 shown in FIG. 2).

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims presented here. Although specific terms are employed herein, they are used in a generic and descriptive sense only and not for purposes of limitation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment of the invention.

We claim:

1. A method of placing multiple stents side-by-side across a single stricture along an unbifurcated length of duct, the method comprising steps of:

directing only a single stent-placement catheter to a location adjacent a stricture along an unbifurcated length of duct to be stent-traversed;

directing only a single wire guide through a wire guide lumen encompassed by at least a lengthwise portion of the stent-placement catheter and through the stricture;

directing a distal end length of the stent-placement catheter through the stricture;

directing a first stent through a lengthwise stent lumen of the stent-placement catheter portion disposed within the stricture and alongside the wire guide, where first stent is advanced distally by a stent pusher and where the wire guide is unencompassed by any portion of the first stent;

moving the stent-placement catheter in a manner that leaves the first stent and the wire guide in place across the stricture; and with the wire guide remaining disposed through the stricture and the stent-placement catheter remaining disposed within or immediately adjacent the stricture, directing a second stent through the stent lumen and through the stricture alongside the wire guide and at least partially alongside, and wholly external of, the first stent, where the second stent is advanced distally by the stent pusher and where the wire guide and the first stent are unencompassed by any portion of the second stent.

2. The method of claim 1, where the at least a lengthwise portion of the catheter through which the wire guide is directed is embodied as a longitudinal wire guide lumen extending through a major length of the stent-placement catheter and configured for operation during a long-wire procedure such that the step of directing a wire guide comprises directing the wire guide through at least a lengthwise portion of the stent-placement catheter's wire guide lumen.

3. The method of claim 1, where the at least a lengthwise portion of the stent-placement catheter through which the wire guide is directed is embodied as a longitudinal wire guide lumen extending through a minor length of the stent-placement catheter and configured for operation during a short-wire procedure such that: the step of directing the wire guide comprises directing the wire guide through at least a lengthwise portion of the wire guide lumen, and the step of directing a wire guide comprises directing the wire guide through at least a lengthwise portion of the stent-placement catheter 's wire guide lumen.

4. The method of claim 1, where the lengthwise stent lumen extends through a major length of the catheter.

5. The method of claim 1, further comprising a step of deploying a third stent at least partially alongside the first stent and the second stent.

6. The method of claim 1, where the stent-placement catheter is configured with a rounded atraumatic distal tip.

7. The method of claim 6, where a distal opening of the lengthwise stent lumen is disposed along a longitudinal side of the stent-placement catheter.

8. The method of claim 1, where a distal opening of the lengthwise stent lumen is disposed along a longitudinal side of the stent-placement catheter.

9. The method of claim 8, where a transition from a longitudinal length of the stent lumen to the distal opening is curved to provide for smooth exit of a stent from the stent lumen.

10. The method of claim 1, where the stricture is located in a biliary duct, and at least one method step is operated via a transesophageal endoscope.

* * * * *